US006984127B2

(12) United States Patent
Lai (10) Patent No.: US 6,984,127 B2
(45) Date of Patent: Jan. 10, 2006

(54) ORTHODONTIC BRACE WITH SELF-RELEASING APPLIANCES

(75) Inventor: Ming-Lai Lai, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 392 days.

(21) Appl. No.: 10/393,095

(22) Filed: Mar. 20, 2003

(65) Prior Publication Data

US 2004/0185410 A1 Sep. 23, 2004

(51) Int. Cl.
  *A61C 3/00* (2006.01)
(52) U.S. Cl. ............................................. 433/8; 433/24
(58) Field of Classification Search .................. 433/24, 433/18, 2, 10, 8
  See application file for complete search history.

(56) References Cited

U.S. PATENT DOCUMENTS

| | | |
|---|---|---|
| 1,991,047 A | 2/1935 | Boyd et al. |
| 3,052,027 A | 9/1962 | Wallshein |
| 3,084,437 A | 4/1963 | Neger |
| 3,327,393 A | 6/1967 | Brader |
| 3,464,112 A | 9/1969 | Silverman et al. |
| 3,464,113 A | 9/1969 | Silverman et al. |
| 3,724,074 A | 4/1973 | Wallshein |
| 3,772,787 A | 11/1973 | Hanson |
| 4,103,423 A | 8/1978 | Kessel |
| 4,149,314 A | 4/1979 | Nonnenmann |
| 4,171,568 A | 10/1979 | Forster |
| 4,197,642 A | 4/1980 | Wallshein |
| 4,248,588 A | 2/1981 | Hanson |
| 4,260,375 A | 4/1981 | Wallshein |
| 4,371,337 A | 2/1983 | Pletcher |
| 4,492,573 A | 1/1985 | Hanson |
| 4,496,318 A | 1/1985 | Connelly, Jr. |
| 4,551,094 A | 11/1985 | Kesling |
| 4,559,012 A | 12/1985 | Pletcher |
| 4,698,017 A | 10/1987 | Hanson |
| 4,712,999 A | 12/1987 | Rosenberg |
| 4,725,229 A | 2/1988 | Miller |
| 4,820,151 A | 4/1989 | Pospisil |
| 4,846,681 A | 7/1989 | Mourany et al. |
| 4,927,362 A | 5/1990 | Snead |
| 5,039,302 A | 8/1991 | Keys |
| 5,094,614 A | 3/1992 | Wildman |

(Continued)

FOREIGN PATENT DOCUMENTS

WO   WO 98/20805   5/1998

(Continued)

OTHER PUBLICATIONS

Voudouris, John C. "Seven Clinical Principles of Interactive Twin Mechanisms", *Journal Clinical Orthodontics, Inc.* 1997, vol. XXXI, No. 1, pp. 55-65.

(Continued)

*Primary Examiner*—Cary E. O'Connor
*Assistant Examiner*—Candice C. Stokes
(74) *Attorney, Agent, or Firm*—James D. Christoff (57) ABSTRACT

An orthodontic brace includes a set of appliances that are connected to respective teeth of the patient. At least some of the appliances include a latch that is operable to release an archwire from the appliance whenever the force exerted by the archwire exceeds a certain value. This value is higher for appliances connected to certain teeth than the value associated with appliances connected to other teeth, in accordance with the particular malocclusion encountered. The brace is constructed to ensure that the goals of the treatment program are carried out in an efficient manner while reducing the likelihood of inadvertent release of the archwire during the course of treatment.

24 Claims, 4 Drawing Sheets

U.S. PATENT DOCUMENTS

| | | |
|---|---|---|
| 5,269,681 A | 12/1993 | Degnan |
| 5,322,435 A | 6/1994 | Pletcher |
| 5,356,289 A | 10/1994 | Watanabe |
| 5,466,151 A | 11/1995 | Damon |
| 5,474,445 A | 12/1995 | Voudouris |
| 5,516,284 A | 5/1996 | Wildman |
| 5,562,444 A | 10/1996 | Heiser et al. |
| 5,613,850 A | 3/1997 | Wildman et al. |
| 5,630,715 A | 5/1997 | Voudouris |
| 5,630,716 A | 5/1997 | Hanson |
| 5,685,711 A | 11/1997 | Hanson |
| 5,711,666 A | 1/1998 | Hanson |
| 5,857,849 A | 1/1999 | Kurz |
| 5,857,850 A | 1/1999 | Voudouris |
| 5,863,199 A | 1/1999 | Wildman |
| 5,890,893 A | 4/1999 | Heiser |
| 5,908,293 A | 6/1999 | Voudouris |
| 5,913,680 A | 6/1999 | Voudouris |
| 5,967,773 A | 10/1999 | Roman et al. |
| 5,971,753 A | 10/1999 | Heiser |
| 6,168,428 B1 | 1/2001 | Voudouris |
| 6,302,688 B1 | 10/2001 | Jordan et al. |
| 6,524,101 B1 | 2/2003 | Phan et al. |
| 6,582,226 B2 | 6/2003 | Jordan et al. |
| 2001/0029008 A1 | 10/2001 | Jordan et al. |
| 2003/0096209 A1* | 5/2003 | Sugiyama et al. ............. 433/8 |
| 2004/0072118 A1 | 4/2004 | Heiser et al. |

FOREIGN PATENT DOCUMENTS

| | | |
|---|---|---|
| WO | WO 02/064052 | 8/2002 |
| WO | WO 02/089693 | 11/2002 |
| WO | WO 03/000151 | 1/2003 |

OTHER PUBLICATIONS

Pending U.S. Appl. No. 10/287,089.

Pending U.S. Appl. No. 10/287,165.

* cited by examiner

ORTHODONTIC BRACE WITH SELF-RELEASING APPLIANCES

BACKGROUND OF THE INVENTION

1. Field of the Invention

This invention relates to a brace or components of a brace used in orthodontic treatment to correct malocclusions. The brace and brace components include orthodontic appliances such as a bracket or buccal tube having a releasable latch for releasably retaining an archwire in an archwire slot of the appliance.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth.

Many types of orthodontic brackets have archwire slots that are open on one side for insertion of the archwire, and bounded on remaining sides by walls or other structure. Brackets that are intended to be bonded to the patient's front tooth surfaces often have archwire slots that are open either on a buccolabial side (i.e., a side facing the patient's cheeks or lips) or an occlusal side (i.e., a side facing the outer tips of the teeth) of the archwire slot. Some brackets, however, are intended to be fixed to the lingual side of the patient's teeth (i.e., the side of the teeth facing the patient's tongue) and typically have an archwire slot that is open on a lingual side or on an occlusal side.

Orthodontists often use ligatures to connect the archwire to the brackets and to urge the archwire into an orientation of seating engagement in the archwire slot. One type of commercially available orthodontic ligature is a small, elastomeric O-ring. Orthodontic O-ring ligatures are installed by stretching the O-ring around small wings (known as "tiewings") that are connected to the bracket body on the gingival side (i.e., the side facing the patient's gingiva or gums) and on the occlusal side of the archwire slot. Once installed, the O-ring ligature extends around the back or lingual side of the tiewings as well as over the labial side of the archwire and urges the archwire toward a fully seated position in contact with a lingual wall of the archwire slot.

Metal ligatures, such as ligatures made of stainless steel, are also used to retain archwires in archwire slots of brackets. Metal ligatures are typically made of a short section of initially straight wire that is subsequently formed into a loop. During installation, the wire ligature is hooked around the tiewings and extended over the labial side of the archwire. End sections of the ligature are then twisted together to close the loop and retain the ligature in place.

Unfortunately, some orthodontists are not entirely satisfied with elastomeric and metal ligatures. Such ligatures are somewhat time-consuming to install, both during initial installation and also during reinstallation whenever replacement of the archwire or ligatures is desired. As can be appreciated, decreasing the amount of time needed for ligation can help to reduce the total time that the practitioner must spend with the patient and consequently decrease the overall costs of orthodontic treatment.

Other disadvantages are also associated with elastomeric and metal ligatures. For example, there have been reports that certain polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of infection.

In an effort to overcome the problems associated with conventional ligatures, a variety of orthodontic brackets have been proposed having various types of latches for coupling the archwire to the bracket. Such brackets are also known as self-ligating brackets. The latch comprises a movable clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, the bracket illustrated in U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latch of these references has a somewhat cylindrical shape and is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

Improved self-ligating orthodontic brackets are described in two pending PCT applications entitled "ORTHODONTIC APPLIANCE WITH SELF-RELEASING LATCH", WO01/22901 and US02/09896. The appliances described in these applications have a latch for retaining an archwire in the archwire slot, and the latch releases the archwire from the archwire slot whenever the archwire exerts a force on the appliance that exceeds a certain minimum value. The minimum value is significantly less than the force required in the same direction to debond the appliance from the tooth, and consequently helps ensure that the appliance will not spontaneously debond from the tooth during the course of treatment.

In certain embodiments of the appliances described in the PCT applications mentioned above, the archwire may be inserted into the archwire slot by pressing the archwire against the latch. The latch is constructed to self-open without the need for hand instruments or other tools. Consequently, such appliances are a great advantage to the practitioner in that the time needed for connecting the archwire to the appliance can be significantly reduced.

However, certain orthodontic patients have teeth that are severely maloccluded. For example, one tooth along the dental arch may be significantly out of alignment with neighboring teeth. As another example, one of the teeth may have shifted in a rotative direction about its long axis to an unsatisfactory orientation. Moreover, one or more teeth may be both out of alignment and rotated about their long axes. Such malocclusions are considered unaesthetic and may adversely affect the normal function of the teeth during mastication.

The orthodontic appliances described in the above-mentioned PCT applications have been found advantageous in the treatment of malocclusions. However, in instances of severe malocclusions as described in the examples above, it may be necessary to bend the portion of the archwire adjacent the maloccluded tooth to a substantial extent in order to seat the archwire in the archwire slots. In some cases, this localized bending can greatly increase the force of the archwire against the latch to such a degree that the latch opens and releases the archwire. The force exerted by the archwire may be much higher in instances where the local bend has a relatively small radius or in instances where the archwire is relatively stiff.

As can be appreciated, inadvertent, premature release of the archwire from the archwire slot of the appliances mentioned above is best avoided if at all possible. If the archwire is inadvertently released, the patient should return to the orthodontist for reinsertion of the archwire so that treatment can be resumed. However, inadvertent release may occur again in the future unless the orthodontist replaces the archwire with an archwire having less stiffness, or alternatively uses a ligature to help secure the archwire in the archwire slot. In either case, the advantages of these appliances are compromised.

SUMMARY OF THE INVENTION

The present invention is directed toward improvements in orthodontic braces that comprise appliances having a self-releasing latch. The latch of each appliance releases the archwire from the archwire slot whenever the archwire exerts a force on the latch that exceeds a certain value. Advantageously, this certain value (or "release value") is higher for certain appliances in comparison to other appliances along the dental arch, so that it is less likely that the archwire is inadvertently released even in instances of severe malocclusions.

Moreover, the efficiency of an orthodontic treatment program may be enhanced when certain teeth are subjected to higher levels of force than the force exerted on other teeth. For example, teeth located in posterior regions of the oral cavity have, in general, larger roots than the roots of teeth located in anterior regions. To maintain approximately the same stress/strain distribution in the periodontal ligament along the dental arch and rate of movement of the teeth, higher forces will, in general, be needed for the larger posterior teeth in comparison to the anterior teeth. Consequently, it is beneficial in certain instances to construct the latch of posterior appliances to provide a higher release value than the release value of anterior appliances.

Varying the release value from one appliance to another provides other advantages as well. For example, the practitioner may elect to limit the maximum amount of force exerted on a tooth by an archwire, as determined by the release value of the latch, so that the periodontal ligament responds to movement of the root or roots in the most effective manner. Limiting the release value also serves to limit the amount of pain that might be experienced by the patient. Additionally, a higher release value may be desired for appliances located next to orthodontic force modules (such as Class II or Class III correctors) that tend to exert a force on the archwire.

In more detail, the present invention in one aspect is directed to an orthodontic brace that comprises a first set of orthodontic appliances for anterior teeth of a dental arch and a second set of orthodontic appliances for posterior teeth of the dental arch. At least one appliance of the first set and at least one appliance of the second set has a base for bonding the appliance to a tooth, a body extending from the base, an archwire slot extending across the body in a generally mesial-distal direction and a latch connected to the body for releasably retaining an archwire in the archwire slot. The latch releases the archwire from the archwire slot whenever the archwire exerts a force on the latch that exceeds a certain value. The certain value is greater for at least one appliance of the second set than the certain value of at least one appliance of the first set.

Another embodiment of the invention is directed to an orthodontic brace comprising a first set of orthodontic appliances and a second set of orthodontic appliances. The brace comprises a central appliance for a central tooth, a lateral appliance for a lateral tooth, a cuspid appliance for a cuspid tooth, a bicuspid appliance for a bicuspid tooth and a second bicuspid appliance for a second bicuspid tooth. Each appliance has a base, a body extending from the base, an archwire slot extending across the body in a generally mesial-distal direction, and a latch connected to the body for releasably retaining an archwire in the archwire slot. The latch releases the archwire from the archwire slot whenever the archwire exerts a force on the latch that exceeds a certain value. The second set includes at least one of the cuspid appliance, the first bicuspid appliance and a lateral appliance, and the first set includes the remaining appliances of the brace. The certain value is greater for at least one appliance of the second set than the certain value of at least one appliance of the first set.

The present invention is also directed toward an orthodontic brace comprising a first set of orthodontic appliances, a second set of orthodontic appliances and an orthodontic archwire connected to the first and second sets of orthodontic appliances. Each appliance has a base, a body extending from the base, an archwire slot extending across the body in a generally mesial-distal direction, and a latch connected to the body for releasably retaining the archwire in the archwire slot. The latch releases the archwire from the archwire slot whenever the archwire exerts a force on the latch that exceeds a certain value. The archwire has a labial side with a concave portion when received in the archwire slots of the appliances. The second set of appliances includes at least one appliance that is adjacent the concave portion of the archwire, and the first set of appliances includes the remaining appliances of the brace. The certain value is greater for at least one appliance of the second set than the certain value of at least one appliance of the first set.

Other aspects of the invention are described in the paragraphs that follow and are illustrated in the accompanying drawings.

DETAILED DESCRIPTION OF THE PREFERRED EMBODIMENTS

Figure 1:
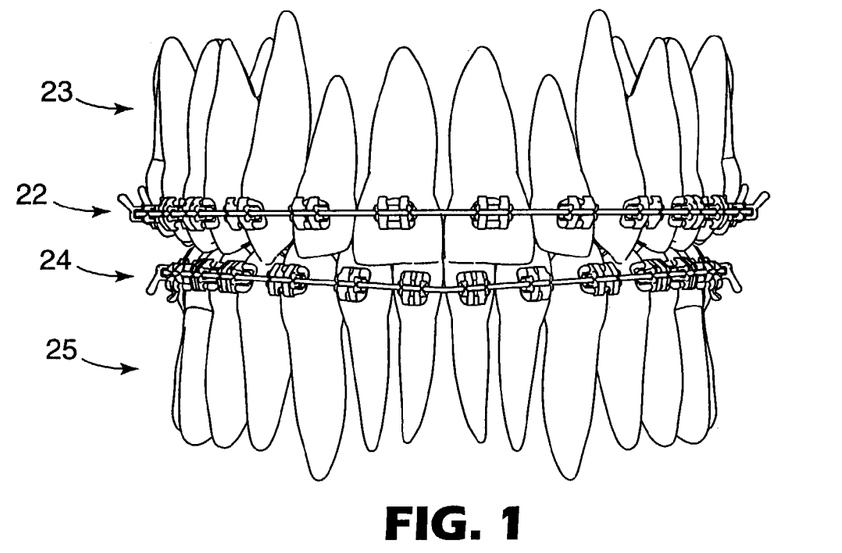
FIG. 1 is a front elevational view showing the teeth of an exemplary patient undergoing orthodontic treatment, wherein orthodontic appliances are affixed to the teeth of the upper and lower jaw and an archwire that has been connected to the appliances associated with each jaw.

FIG. 1 illustrates an example of an oral cavity of an orthodontic patient who is undertaking orthodontic therapy. The patient has a first orthodontic brace 22 that is connected to the teeth of the upper dental arch 23 and a lower orthodontic brace 24 that is connected to the teeth of the lower dental arch 25. Each brace 22, 24 includes a set of orthodontic appliances along with an archwire that is received in slots of the appliances, as will be described in more detail below.

Figure 2:
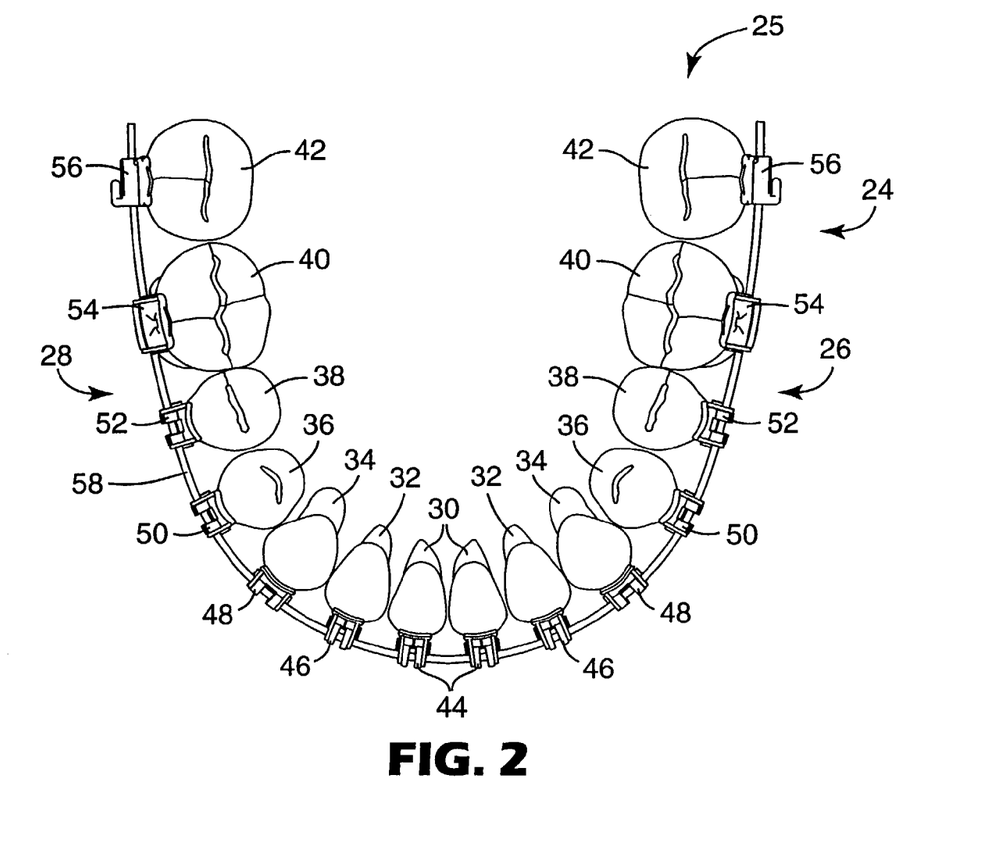
FIG. 2 is an enlarged plan view of the teeth of the lower jaw of the oral cavity illustrated in FIG. 1, also showing the appliances and the associated archwire.

FIG. 2 is an enlarged view of the lower dental arch 25 along with the lower brace 24, looking in a downwardly direction toward the outer or occlusal tips of the teeth. The lower dental arch includes a left quadrant 26 and a right quadrant 28. Each of the quadrants 26, 28 includes a central incisor tooth 30, a lateral incisor tooth 32, a cuspid tooth 34, a lower first bicuspid tooth 36 and a second bicuspid tooth 38. In addition, each of the quadrants 26, 28 includes a first molar tooth 40 and a second molar tooth 42.

The illustration of the lower dental arch 25 shown in FIG. 2 is only one example of dentition, and many variations are possible. For example, the patient may lack one or more of the illustrated teeth, as may occur in adolescent patients when some of the permanent teeth have not yet erupted. Alternatively, one or more teeth may have been removed prior to orthodontic treatment in order to reduce crowding, especially in instances where the overall size of the dental arch is relatively small. Moreover, the lower dental arch 25 may include third molar teeth, also known as wisdom teeth, which are not illustrated in the drawing.

The lower brace 24 includes a set of appliances connected to the teeth of the lower quadrants 26, 28. In particular, the lower brace 24 in each of the lower quadrants 26, 28 includes a central incisor appliance 44 that is coupled to the central incisor tooth 30, a lateral incisor appliance 46 that is connected to the lateral incisor tooth 32 and a cuspid appliance 48 that is connected to the cuspid tooth 34. The lower brace 24 also includes, along each quadrant 26, 28, a first bicuspid appliance 50 that is coupled to the first bicuspid tooth 36, a second bicuspid appliance 52 that is connected to the second bicuspid tooth 38, a first molar appliance 54 that is connected to the first molar tooth 40 and a second molar appliance 56 that is connected to the second molar tooth 42.

Optionally, one or more of the appliances described above may be omitted in accordance with the preference of the orthodontist. For example, if the second molar teeth 56 have not yet fully erupted, the orthodontist may elect to omit the second molar appliances 56, at least during the early stages of treatment. As another option, the central incisor appliance 44 and the lateral incisor appliance 46 may be identical and instead called "lower anterior appliances".

The lower brace 24 also includes an archwire 58 made of a resilient material. Suitable materials include, for example, metallic materials such as alloys of nitinol and stainless steel. The archwire 58 has a generally overall "U"-shaped configuration and extends along both of the quadrants 26, 28.

Figures 3, 4:
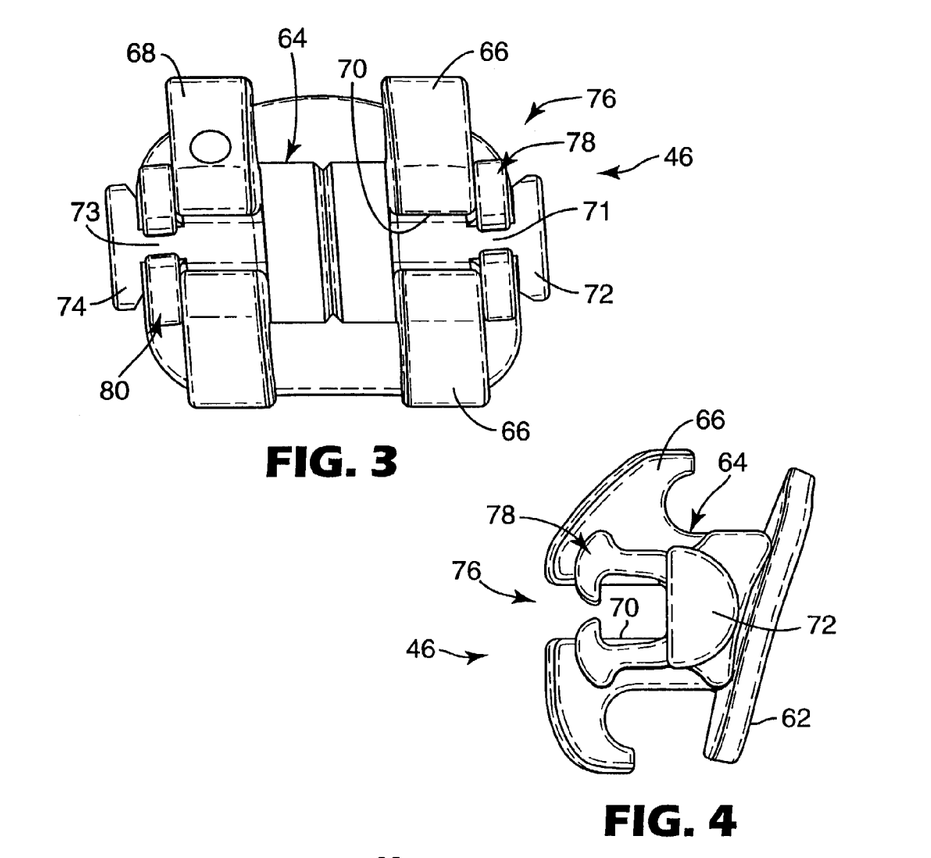
FIG. 3 is an enlarged front elevational view of one of the appliances depicted in FIGS. 1 and 2.
FIG. 4 is a side elevational view of the appliance shown in FIG. 3.
Figure 5:
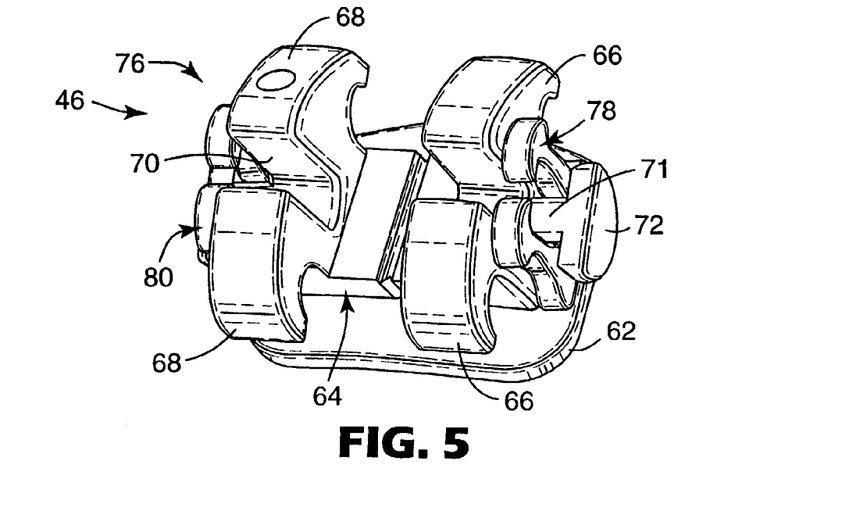
FIG. 5 is a perspective view of the appliance shown in FIGS. 3 and 4.

A representative example of a self-releasing appliance is the appliance 60 shown in enlarged view in FIGS. 3–5. The appliance 60 as depicted is particularly suitable for use with an upper central tooth, but is generally similar to remaining appliances such as the appliances 44–52.

The appliance 60 includes a base 62 for bonding the appliance 60 directly to the enamel of an upper central tooth by use of an adhesive. Preferably, the base 62 has an outwardly-facing concave compound contour that matches the convex compound contour of the tooth surface. Optionally, the base 62 may be provided with grooves, particles, recesses, undercuts, a chemical bond enhancement material or any other material or structure or any combination of the foregoing that facilitates bonding the appliance 60 directly to the tooth surface.

A body 64 extends outwardly from the base 42 in a generally buccolabial direction. The body 64 includes a spaced-apart pair of mesial tiewings 46 and a pair of spaced-apart distal tiewings 68. An archwire slot 70 extends across the body 64 in a generally mesial-distal direction and between the space presented by the pair of mesial tiewings 66 and the space presented between the pair of distal tiewings 68. Optionally, the tiewings 66, 68 may be omitted.

The body 64 also includes a mesially extending support 71 that is connected to an outermost mesial flange 72 and a distally extending support 73 that is connected to an outermost distal flange 74. Each of the flanges 72, 74 has a somewhat semi-circular configuration in elevational view, although other shapes are also possible. Preferably, the flanges 72, 74 are integral with the supports 71, 73 respectively although as another option the flanges 72, 74 may be affixed to the remaining portions of the body 64 after first being separately manufactured.

The appliance 60 also includes a latch 76 that is connected to the body 64 for releasably retaining an archwire in the archwire slot 70. In this embodiment, the latch 76 includes a mesial clip 78 and a distal clip 80 although other alternatives are also possible. For example, the latch 76 could have only a single clip that is optionally located in the space between the pair of mesial tiewings 66 and the pair of distal tiewings 68.

Figure 6:
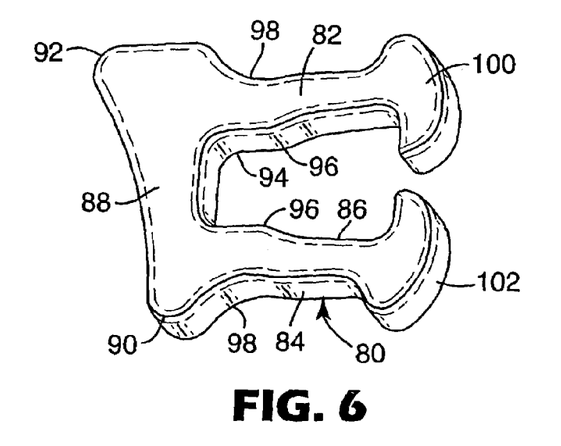
FIG. 6 is an enlarged perspective view of one component of a latch of the appliance illustrated in FIGS. 3–5.
Figure 7:
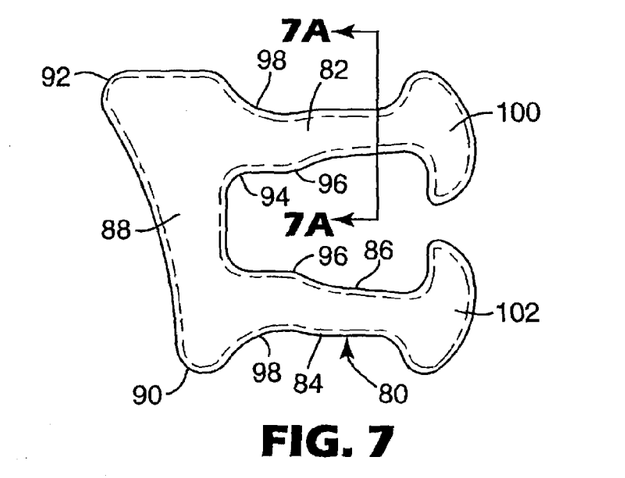
FIG. 7 is an enlarged side elevational view of the latch component shown in FIG. 6.

The distal clip 80 is shown alone in FIGS. 6 and 7 and has an overall, generally "C"-shaped configuration. The distal clip 80 includes a first section 82 and a second section 84 that is opposed to the first section 82. In their normal, relaxed configuration, the first section 82 and the second section 84 extend in generally parallel directions. The first section 82 is spaced apart from the second section 84 to present a region 86 for receiving an archwire.

The clip 80 also includes a third section 88 that interconnects the first section 82 and the second section 84. When assembled to the body 44, the third section 88 extends in a generally occlusal-gingival direction along the buccolabial surface of the base 62 as can be appreciated by reference to FIG. 4. The third section 88 extends beyond the first section 82 and the second section 84 in an occlusal-gingival direction and terminates at a rounded, protruding outermost occlusal corner 90 and a rounded, protruding outermost gingival corner 92.

Preferably, and as shown in FIG. 4, the corners 90, 92 contact the buccolabial side of the base 62 when the clip 80 is assembled to the body 64. However, a middle portion of the third section 88 is slightly spaced from the buccolabial side of the base 62. Such construction ensures that the clip 80 contacts the base 62 at two locations and does not unduly rock about a mesial-distal reference axis during use.

As illustrated in FIGS. 6 and 7, the clip 80 also includes a recess 94 that communicates with the archwire-receiving region 86. The recess 94 is smaller than the region 86 in directions parallel to the direction of extension of the third section 88, which in turn is generally parallel to an occlusal-gingival reference axis. At the entrance to the recess 94, the first and second sections 82, 84 present a pair of opposed protrusions 96 that extend inwardly toward each other. The opposite side of the first and second sections 82, 84 also each present a notch 98 that is opposed to the respective, adjacent protrusion 96.

The clip 80 also has a pair of arm portions 100, 102 that extend inwardly toward each other. A buccolabial edge of the arm portions 100, 102 is smoothly curved in an arc about a mesial-distal reference axis. For the arm portion 100, this smooth outer curve extends in a gingival direction beyond the gingival side of the first section 82. For the arm portion 102, the smooth outer curve extends in an occlusal direction beyond the occlusal side of the second section 84.

The clip 80 is shown in its normal, relaxed orientation in FIGS. 3–7. However, the arm portions 100, 102 are movable away from each other in order to admit an archwire into the archwire-receiving region 86 when desired. To this end, the first and second sections 82, 84 bend in respective arcs away from each other in order to enable the arm portions 100, 102 to move apart from each other.

The smooth, outer curve on the buccolabial side of the arm portions 100, 102 enables the clip 80 to open and admit an archwire into the region 86 by pressing an archwire against the outer curved edges of the arm portions 100, 102. As pressure is exerted on the curved edges by the archwire, the first and second sections 82, 84 deflect away from each other in order to admit the archwire into the region 86. Once the archwire is received in the region 86, the inherent resiliency of the clip 80, and particularly the resiliency of the first and second sections 82, 84, enables the arm portions 100, 102 to spring back toward each other and to their normal, relaxed configuration as shown in the drawings in order to retain the archwire in the archwire slot 70.

Figure 7A:
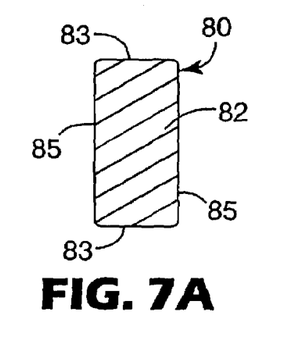
FIG. 7a is an enlarged cross-sectional view taken along lines 7a—7a of FIG. 7.

FIG. 7a is a cross-sectional view of the first section 82 of the clip 80. As shown, the shape of this cross-section is rectangular. The first section 82 has a longitudinal axis extending generally along a buccolabial-lingual reference axis, and includes occlusal and gingival walls 83 as well as mesial and distal walls 85. The walls 83, 85 are substantially perpendicular to each other as is preferred for appliances having a zero angulation. A similar orientation of walls is present in other regions of the clip 80, including the second and third sections 84, 88 as well as in the arm portions 100, 102. Although not appreciably shown in the drawings, the intersections between the walls are rounded.

Figure 7B:
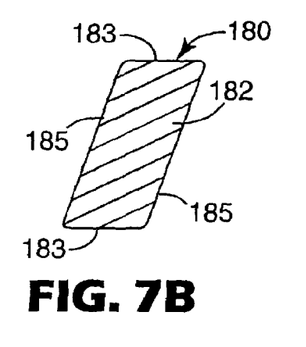
FIG. 7b is a view somewhat similar to FIG. 7a except that another embodiment of the invention is illustrated.

FIG. 7b is a view somewhat similar to FIG. 7a, but showing a section of a clip 180 according to another embodiment of the invention. The clip 180 has a shape, when viewed in a mesial or distal direction, that is similar to the shape of the clip 80. However, in this embodiment, a first section 182 of the clip 180 has occlusal and gingival walls 183 that are oriented at an angle other than 90 degrees relative to mesial and distal walls 185. A similar orientation of walls is present at other regions of the clip 180, including in a second and third section as well as in arm portions of the clip.

The cross-sectional shape of the clip 180 resembles a rhomboid or a parallelogram having no right angles. Such construction is a particular advantage when used in combination with appliances known as "angulated" appliances having an archwire slot that extends at a similar angle relative to mesial and distal sides of tiewings and/or the appliance body. In these instances, the total area occupied by a clip may remain the same without unduly decreasing its cross-sectional area or its resultant strength and fatigue life.

To assemble the clip 80 to remaining components of the appliance 60, the clip 80 is preferably put in place before the base 62 is affixed to the body 64. During assembly, the clip 80 is moved in a buccolabial direction in the space between the distal flange 74 and the remaining portions of the body 64 and the arm portions 100, 102 are spread apart a distance sufficient to enable the support 73 to be received in the region 86. The clip 80 is then moved further in a buccolabial direction until such time as the support 73 is received in the recess 94.

Next, and after the clip 78 is installed in a similar manner, the base 62 is affixed to the body 64 by a suitable process such as brazing or welding (including laser welding). Once the base 62 is affixed to the body 64, the clip 80, and particularly the third section 88, is captured between the support 73 and the base 62 and is thereafter retained in place. At this time, the region 86 is aligned with the archwire slot 70 as can be appreciated by comparison of FIG. 3 and FIG. 4.

The clip 80 (including the first and second sections 82, 84) is sufficiently stiff to retain the archwire in the archwire slot 70 during the course of treatment so long as the forces exerted by the archwire on the appliance 46 are below a certain minimum value in a generally buccolabial direction (more particularly, in a direction opposite to the direction of insertion of the archwire into the archwire slot 70). However, whenever the forces exerted by the archwire on the appliance 46 in the same direction are greater than the minimum value, as might occur when unexpectedly high forces are encountered, the first and second sections 82, 84 deflect outwardly and the arm portions 100, 102 move apart from each other to open the clip 78 and enable the archwire to be released from the archwire slot 70.

Preferably, the minimum value for self-release (i.e., self-opening) of the latch 76 is substantially less than the force required in the same direction to debond the appliance 60 from the associated tooth. The minimum value for self-release of the latch 76 is preferably less than about one-half of the force required in the same direction to debond the appliance 60 from the associated tooth. For example, if the expected bond strength of the adhesive bond between the appliance 60 and the associated tooth is 16 lbs (7.2 kg) in a buccolabial direction, the latch 76 is constructed to self-release the archwire whenever the archwire exerts a force in the same buccolabial direction on the appliance 60 that is somewhat greater than about 8 lbs (3.6 kg).

To determine the force to release the latch 76, a section of archwire is selected having an area in longitudinally transverse sections that is complemental to (i.e., substantially fills) the cross-sectional area of the archwire slot 70. Next, a sling is constructed and is connected to the archwire section at locations closely adjacent, but not in contact with the mesial flange 72 and the distal flange 74. Optionally, the sling is welded or brazed to the archwire section. Next, the sling is pulled away from the appliance 60 while the appliance 60 is held in a stationary position, taking care to ensure that the longitudinal axis of the archwire section does not tip relative to the longitudinal axis of the archwire slot 70. The force to release the latch 76 may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

The self-releasing latch 76 is a benefit to the practitioner, in that the likelihood of spontaneous debonding of the appliance 60 from the tooth is substantially reduced. For example, if the practitioner attempts to place a relatively large archwire in the archwire slot 70 and the latch 76 self-releases as soon as the practitioner releases the archwire, the practitioner can then use an archwire with less stiffness in its place so that the appliance 46 is not detached from the tooth surface. As another example, if the archwire is initially held in the archwire slot 76 by the arm portions 100, 102 and the archwire subsequently exerts a larger force on the appliance 46 (as may occur, for example, when the archwire encounters a hard object such as when the patient is chewing relatively hard food), the arm portions 100, 102 spread apart to their slot-open positions to release the archwire so that the appliance 60 does not debond from the tooth. Treatment can then be resumed by merely re-engaging the archwire in the archwire slot 70 without the need to rebond the base 62 to the associated tooth.

Preferably, the distance between the opposed ends of the arm portions 100, 102 is less than the overall occlusal-gingival dimension of the smallest archwire expected to be used during the course of treatment. The archwire need not fill the archwire slot 70 and flatly engage the wall portions defining the archwire slot 70 in all instances. For example, a somewhat smaller wire, and perhaps an archwire having a circular cross-sectional shape, may be used during a portion of the treatment program. The distance between the opposed ends of the arm portions 100, 102 is preferably selected so that a variety of archwires of different cross-sectional configurations may be used in connection with the appliance 46.

Preferably, the distal clip 80 is identical to the mesial clip 78. Optionally, however, it is possible to construct the clips 78, 80 somewhat differently to address certain circumstances. For example, if a malpositioned tooth is initially oriented such that its mesial side is rotated in a lingual direction, it may be desirable to increase the stiffness of the mesial clip 78 so that a somewhat greater force is needed to release the archwire from the archwire slot 70 in comparison to the force needed to release the archwire from the distal clip 80. Other options are also possible.

Optionally, the spring clips 78, 80 are cut from a flat section of metallic stock material. Suitable metallic materials include shape memory alloys such as alloys of nitinol and beta-titanium. The clips 78, 80 may be cut from the stock material using a stamping, die cutting, chemical etching, EDM (electrical discharge machining), laser cutting or water jet cutting process. As another option, the clips 78, 80 could be formed and then heat treated to set their shapes.

As presently preferred, the clips 78, 80 are made from flat annealed superelastic material (such as nitinol) having a pickled surface. Preferred nitinol materials have a nickel content of 55.97% by weight and an $A_f$ of 10°±5° C. The nitinol is cold worked to 37.5% and has a thickness in the range of about 0.012 in. (0.3 mm) to about 0.016 in. (0.4 mm). The clips 78, 80 are first cut in a rough cutting EDM process, then cut along their edges for an additional one or more times using an EDM process in order to smooth the edges. Alternatively, a laser cutting process or chemical etching process could be used to make the clips 78, 80. Preferably, the clips 78, 80 are constructed so that the longitudinal direction of the clip material, or the principal direction of grain flow of the clip material, is substantially parallel to the direction of extension of the first and second sections 82, 84 (i.e. a generally buccolabial direction).

Subsequent to the EDM, laser cutting or chemical etching process, the clips 78, 80 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size 3/16×3/8 (4.7 mm×9.5 mm), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. T1121 Pickling Solution from Aya International of Los Angeles, Calif.

Advantageously, the shape of the clip 78 as shown in FIGS. 6 and 7 reduces maximum strain and stress during opening and closing movements so that the expected useful life of the clip 78 is increased. Further details regarding this aspect, along with other alternative constructions of the latch 76 and/or the appliance 60, are described in applicant's pending U.S. patent application Ser. No. 10/287,089, filed Nov. 4, 2002 and entitled "ORTHODONTIC APPLIANCE WITH FATIGUE-RESISTANT ARCHWIRE RETAINING LATCH", the disclosure of which is expressly incorporated by reference herein.

The appliances 44–52 are somewhat similar to the appliance 60, and consequently a detailed description of the similar features need not be repeated. Preferably, however, certain other features are modified or adapted to better function with the associated tooth. For example, the curvature of the base is preferably changed to match the curvature of the corresponding tooth. Additionally, the overall width of the appliance in the mesial-distal direction may be increased or decreased in corresponding relationship to the width of the associated tooth. Furthermore, each appliance is constructed with torque and angulation values that are appropriate for the corresponding tooth for the proposed treatment plan.

Optionally, the first molar appliance 54 and the second molar appliance 56 are somewhat similar to the appliances 44–52 described above. As another option, one or both of the molar appliances 54, 56 is similar to the appliances described in applicant's pending U.S. patent application Ser. No. 10/287,165, filed Nov. 4, 2002 and entitled "MOLAR APPLIANCE FOR ORTHODONTIC THERAPY", the disclosure of which is expressly incorporated by reference herein. As yet another option, one or both of the molar appliances 54, 56 may comprise appliances known as buccal tubes, such as the buccal tube appliances described in U.S. Pat. Nos. 4,820,151 and 4,927,362.

The appliances 44, 46, 48 associated with the left and right quadrants 26, 28 comprise a first set of appliances for the anterior teeth (i.e., central, lateral and cuspid teeth) of the lower dental arch. The appliances 50, 52 and 54 associated with the lower left and right quadrants 26, 28 comprise a second set of appliances for the posterior teeth (i.e., bicuspid and molar teeth) of the lower dental arch. As indicated above, each appliance 44–52 includes a latch for releasably retaining the archwire 58 in the archwire slot. The latch releases the archwire from the archwire slot whenever the archwire exerts a force on the latch that exceeds a certain value, also known as a release value, or "R". The release value is greater for at least one appliance of the second set (i.e., the set of appliances for the posterior teeth) than the release value of at least one appliance of the first set (i.e., the set of appliances for the anterior teeth).

Additionally, for each quadrant, the release value is greater for at least one of the cuspid appliance 48, the first bicuspid appliance 50 and the lateral incisor appliance 46 than the release value of at least one of the central incisor appliance 44 and the second bicuspid appliance 52. The cuspid teeth 48 are frequently out of alignment with adjacent teeth of the dental arch. Moreover, the radius of curvature of the archwire 58 is often smaller in regions adjacent the cuspid tooth 34. As a result, the archwire 58 tends to exert a greater force on the latch of the appliances 46, 48 and 50 than the remaining appliances of the dental arch.

The release value as described above is preferably greater for at least one of the appliances adjacent the regions of the archwire 58 where the radius of curvature of the archwire 58 is relatively small in comparison to other regions of the archwire 58. Such construction helps to ensure that the archwire 58 does not unintentionally release from the latches of the associated appliances.

Figure 8:
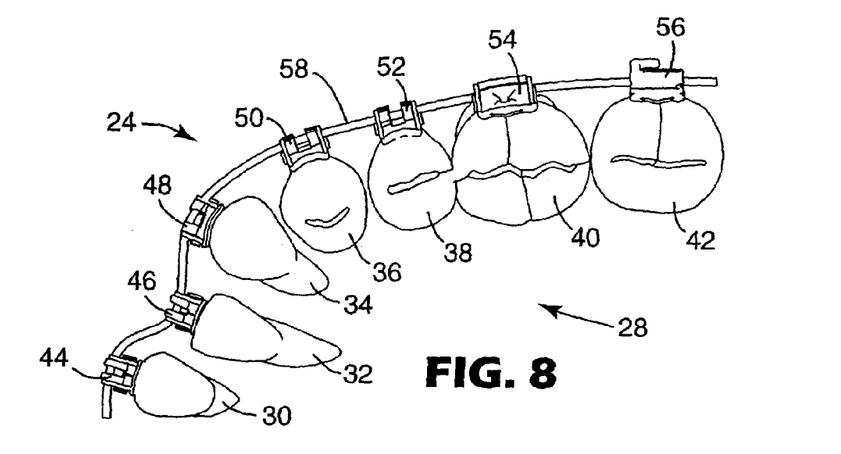
FIG. 8 is an enlarged plan view of a quadrant of the lower dental arch shown in FIG. 3, except that the teeth have been re-arranged to show one example of a malocclusion that might be encountered in a patient undergoing orthodontic treatment.
Figure 9:
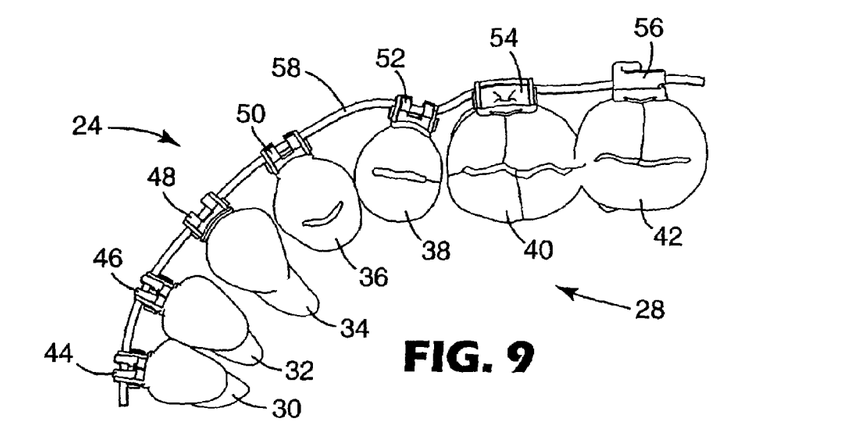
FIG. 9 is a view somewhat similar to FIG. 8 except showing another type of malocclusion that might be encountered.
Figure 10:
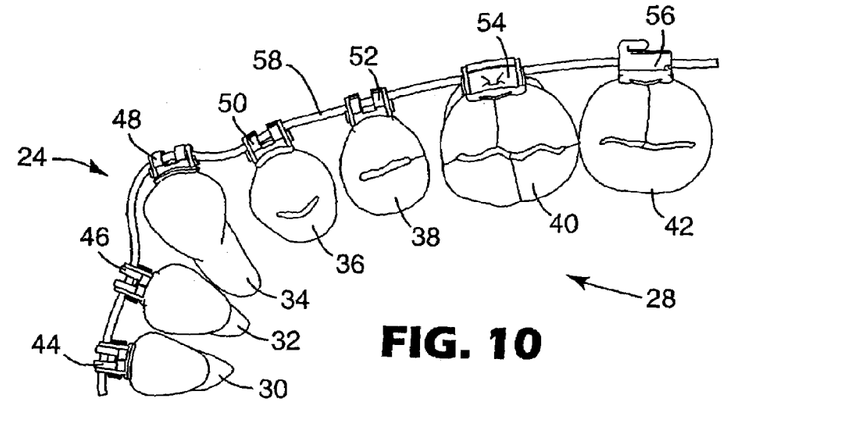
FIG. 10 is a view somewhat similar to FIGS. 8 and 9 except showing yet another example of a malocclusion that might be encountered during orthodontic treatment.

FIGS. 8–10 represent three examples of malocclusions that might be encountered during the course of treatment. In FIG. 8, the lateral incisor tooth 32 is not in alignment with remaining teeth 30, 34–42 of the lower right quadrant 28. Instead, the lateral incisor tooth 32 is located in a lingual direction (i.e., in a direction toward the patient's tongue) from its desired location. As part of treatment, the orthodontist could use the lower brace 24 to bring the lateral incisor tooth 32 into a position of alignment with remaining teeth, so that the lower quadrants 26, 28 form a smooth, arch-shaped curve.

As can be appreciated by reference to FIG. 8, the labial side of the archwire 58 assumes a concave configuration in the vicinity of the lateral incisor appliance 46 when the latch of the appliance 46 has engaged the archwire 58. This concave configuration presents relatively sharp bends in the archwire 58, and the inherent resiliency or "restoring force" of the archwire 58 tends to exert a significant force on the latch of the appliance 46. The restoring force tends to shift the archwire 58 back to its normally arch-shaped configuration that resembles a smooth curve matching the desired final shape of the dental arch.

Consequently, the release value for the latch of the appliance 46 in this example is preferably higher than what might otherwise be desired. For instance, if the lateral incisor tooth 32 was in alignment with the teeth 30, 34–42, the force exerted by the archwire 58 on the latch of the appliance 46 would be substantially smaller. However, when the tooth 32 is out of alignment as shown in FIG. 8, the inherent resiliency of the archwire 58 tends to urge the archwire 58 against the latch 46 with significant force, and consequently a higher release value is desired in order to avoid inadvertent release of the archwire 58 from the appliance 46.

In the example of FIG. 9, all of the teeth 30–42 of the lower right quadrant 28 are in general alignment. However, the second bicuspid tooth 38 has erroneously rotated about its long axis in a clockwise direction viewing FIG. 9. The long axis is generally perpendicular to the plane of the paper in FIG. 9. In this example, one of the goals of orthodontic treatment might be to rotate the second bicuspid tooth 38 about its long axis in a counter-clockwise direction viewing FIG. 9.

When the archwire 58 is seated in the slots of the appliances 44–56 in the example of FIG. 9, the archwire 58 assumes a relatively sharp bend adjacent the distal side of the appliance 52. This relatively sharp bend causes the archwire 58 to exert a substantial force on the distal clip of the latch of the appliance 52. Consequently, the release value of the distal clip for the appliance 52 is preferably higher than what might otherwise be desired.

Although the concave bend of the archwire 58 in the example of FIG. 9 is relatively close to the mesial clip of the appliance 54 and the mesial clip of the appliance 52, the archwire 58 in those locations does not bear against the latch in the configuration as depicted. Instead, the archwire 58 bears against the bottom of the archwire slot. As a result, the mesial clips of the appliances 52, 54 need not be provided with a relatively high release value.

In FIG. 10, the cuspid tooth 34 is out of alignment with teeth 30–32 and 36–42. The cuspid tooth 34 is located in a buccolabial direction (i.e., in a direction toward the patient's lips or cheeks) relative to its final desired position. In addition, the cuspid tooth 34 has also rotated about its long axis in a clockwise direction (viewing FIG. 10) relative to its desired orientation. In this example, one of the goals of orthodontic treatment is to shift the cuspid tooth 34 in a lingual direction and also about its long axis in a counter clockwise direction.

When the archwire 58 is seated in the slots of the appliances 44–56 as depicted in FIG. 10, the labial side of the archwire 58 assumes a concave configuration in areas adjacent the appliances located next to the cuspid appliance 48, namely the appliance 46 and the appliance 50. This concave bend tends to exert a substantial force on the adjacent clip (i.e., the mesial clip) of the latch of the appliance 50, and also on the adjacent clip (i.e., the distal clip) of the latch of the appliance 46. As a result, a somewhat higher release value is desired for those clips in comparison to remaining clips of the appliances 44–56.

In the example of FIG. 10, the archwire 58 is also bent to a substantial extent in areas adjacent the appliance 48. However, the opposite curve of the archwire 58 in this area (i.e., the labial side of the archwire 58 is bent in a convex configuration in this area) causes the archwire 58 to bear against the bottom of the archwire slot and not against the latch of the appliance 48. As such, the clips of the latch of the appliance 48 need not have a relatively high release value.

In general, the release value need not be increased in instances where the tooth is subjected to torque movements (i.e., movement of the tooth by rotation of its long axis in a buccal-lingual direction) or tipping movement (i.e., movement of the tooth by rotation of its long axis in a mesial-distal direction). During torquing and tipping movements, the archwire bears against the sides of the archwire slot and does not typically bear against the latch. Additionally, when the tooth is subject to lateral movement in a lingual direction, the archwire tends to bear against the bottom of the slot (i.e., the lingual side of the archwire slot). Also, during leveling movements in directions along the long axis of the tooth, the archwire bears against the sides of the archwire slot. In these four instances, a higher release value is unnecessary. In general, it is preferred not to increase the release value unless necessary because a higher release value increases the likelihood that the appliance will be unintentionally debonded from the tooth. Additionally, a higher release value may impair the blood flow in the periodontal ligament and reduce tooth movement, or increase the likelihood of root resorption. However, a higher release value may be desired if a force module (such as a Class II or Class III corrector) is nearby, or in instances where the tolerances of the components cannot be tightly controlled.

Table 1 sets out preferred, more preferred and most preferred release values for the latch of appliances of the upper and lower dental arches. However, these values may vary in accordance with the malocclusion encountered. Additionally, it may be desired to increase the following values by a factor of approximately 50 percent in instances where the latch of the appliances consists of a single clip instead of the latches with two clips illustrated in the drawings.

TABLE I

| Appliance | R, Preferred | R, More preferred | R, Most preferred |
|---|---|---|---|
| Appliances For Lower Dental Arch Release Force ("R") in Kg | | | |
| Central Incisor | 1.36 | 0.68 | 0.45 |
| Lateral Incisor | 1.70 | 0.85 | 0.57 |
| Cuspid | 2.05 | 1.02 | 0.68 |
| First Bicuspid | 1.70 | 0.85 | 0.57 |
| Second Bicuspid | 2.05 | 1.02 | 0.68 |
| First Molar | 2.39 | 1.19 | 0.80 |
| Second Molar | 2.39 | 1.19 | 0.80 |
| Appliances For Upper Dental Arch Release Force ("R") in Kg | | | |
| Central Incisor | 1.70 | 0.85 | 0.57 |
| Lateral Incisor | 1.70 | 0.85 | 0.57 |
| Cuspid | 2.05 | 1.02 | 0.68 |
| First Bicuspid | 1.70 | 0.85 | 0.57 |
| Second Bicuspid | 2.05 | 1.02 | 0.68 |
| First Molar | 2.39 | 1.19 | 0.80 |
| Second Molar | 2.39 | 1.19 | 0.80 |

The release value may be altered by one or more of a variety of methods during construction of the appliances. For example, and in connection with the latch 76 shown in FIGS. 3–7, the overall length of the first section 82 and the second section 84 (i.e., in a horizontal direction viewing FIG. 7) may be shortened in order to increase the release value. As another option, the width or thickness of the sections 82, 84 (i.e., in a vertical direction viewing FIG. 7 or in a direction looking toward the plane of the paper in FIG. 7, respectively) may be increased in order to increase the release value.

Other options are also possible. For example, the release value may be increased by lowering the temperature of heat treatment of the clip 78 (when made of nitinol) and/or by increasing the amount of cold working carried out on the clip 78. As another option, the composition of the clip 78 may be changed. If, for example, the clip 78 is made of nitinol, the activation temperature or "$A_f$", may be lowered in order to increase the release value. Alternatively, a clip made of a stiffer material or made with an increased thickness may be provided to increase the release value.

The examples described above are intended to exemplify the various aspects and benefits of the invention. However, those skilled in the art may recognize that a number of variations and additions to the constructions described above may be made without departing from the spirit of the invention. Accordingly, the invention should not be deemed limited to the specific embodiments set out above in detail, but instead only by a fair scope of the claims that follow along with their equivalents.

What is claimed is:

1. An orthodontic brace comprising a first set of orthodontic appliances for anterior teeth of a dental arch and a second set of orthodontic appliances for posterior teeth of the dental arch, wherein at least one appliance of the first set and at least one appliance of the second set has a base for bonding the appliance to a tooth, a body extending from the base, an archwire slot extending across the body in a generally mesial-distal direction, and a latch connected to the body for releasably retaining an archwire in the archwire slot, wherein the latch releases the archwire from the archwire slot whenever the archwire exerts a force on the latch that exceeds a certain value, wherein the certain value is greater for at least one appliance of the second set than the certain value of at least one appliance of the first set.

2. An orthodontic brace according to claim 1 wherein the brace includes a force module, and wherein at least one appliance of the second set is located next to the force module.

3. An orthodontic brace according to claim 1 wherein each latch comprises a mesial clip and a distal clip, each clip having an overall, generally "C"-shaped configuration and comprising a first section, a second section opposed to the first section and a third section interconnecting the first section and the second section, each clip also having a first arm portion connected to the first section remote from the third section and a second arm portion connected to the second section remote from the third section, and wherein the first section and the second section of the mesial clip and the distal clip of the at least one appliance of the second set have a thickness that is greater than the thickness of the first section and the second section of the at least one appliance of the first set.

4. An orthodontic brace according to claim 1 wherein each latch comprises a mesial clip and a distal clip, each clip having an overall, generally "C"-shaped configuration and comprising a first section, a second section opposed to the first section and a third section interconnecting the first section and the second section, each clip also having a first arm portion connected to the first section remote from the third section and a second arm portion connected to the second section remote from the third section, and wherein the first section and the second section of the mesial clip and the distal clip of the at least one appliance of the second set have a width that is greater than the width of the first section and the second section of the at least one appliance of the first set.

5. An orthodontic brace according to claim 1 wherein each latch is made of a material having a certain composition, and wherein the composition of the latch of at least one appliance of the second set is different of the composition of the latch of the at least one appliance of the first set.

6. An orthodontic brace according to claim 1 wherein each latch is made of a material subjected to heat treatment, and wherein the heat treatment of the latch of the at least one appliance of the second set is carried out at a different time and/or temperature than the heat treatment of the latch of the at least one appliance of the first set.

7. An orthodontic brace according to claim 1 wherein each latch is made of a material that has been subjected to cold working, and wherein the cold working of the latch of the at least one appliance of the second set is carried out for a higher percentage of cold working than the percentage of the cold working of the latch of the at least one appliance of the first set.

8. An orthodontic brace according to claim 1 wherein the brace includes an orthodontic archwire connected to at least some of the appliances of the first set and the second set, wherein the archwire has a labial side with a concave portion when received in the archwire slots of the appliances, and wherein the certain value is greater for at least one appliance adjacent the concave portion of the archwire than the certain value of at least one remaining appliance of the brace.

9. An orthodontic brace comprising a first set of orthodontic appliances and a second set of orthodontic appliances, the base comprising a central appliance for a central tooth, a lateral appliance for a lateral tooth, a cuspid appliance for a cuspid tooth, a first bicuspid appliance for a first bicuspid tooth and a second bicuspid appliance for a second bicuspid tooth, wherein each appliance has a base, a body extending from the base, an archwire slot extending across the body in a generally mesial-distal direction, and a latch connected to the body for releasably retaining an archwire in the archwire slot, wherein the latch releases the archwire from the archwire slot whenever the archwire exerts a force on the latch that exceeds a certain value, wherein the second set includes at least one of the cuspid appliance, the first bicuspid appliance and the lateral appliance, wherein the first set includes the remaining appliances of the brace, and wherein the certain value is greater for at least one appliance of the second set than the certain value of at least one appliance of the first set.

10. An orthodontic brace according to claim 9 wherein the brace includes a force module, and wherein at least one appliance of the second set is located next to the force module.

11. An orthodontic brace according to claim 9 wherein each latch comprises a mesial clip and a distal clip, each clip having an overall, generally "C"-shaped configuration and comprising a first section, a second section opposed to the first section and a third section interconnecting the first section and the second section, each clip also having a first arm portion connected to the first section remote from the third section and a second arm portion connected to the second section remote from the third section, and wherein the first section and the second section of the mesial clip and the distal clip of the at least one appliance of the second set have a thickness that is greater than the thickness of the first section and the second section of the at least one appliance of the first set.

12. An orthodontic brace according to claim 9 wherein each latch comprises a mesial clip and a distal clip, each clip having an overall, generally "C"-shaped configuration and comprising a first section, a second section opposed to the first section and a third section interconnecting the first section and the second section, each clip also having a first arm portion connected to the first section remote from the third section and a second arm portion connected to the second section remote from the third section, and wherein the first section and the second section of the mesial clip and the distal clip of the at least one appliance of the second set have a width that is greater than the width of the first section and the second section of the at least one appliance of the first set.

13. An orthodontic brace according to claim 9 wherein each latch is made of a material having a certain composition, and wherein the composition of the latch of at least one appliance of the second set is different of the composition of the latch of the at least one appliance of the first set.

14. An orthodontic brace according to claim 9 wherein each latch is made of a material subjected to heat treatment, and wherein the heat treatment of the latch of the at least one appliance of the second set is carried out at a different time and/or temperature than the heat treatment of the latch of the at least one appliance of the first set.

15. An orthodontic brace according to claim 9 wherein each latch is made of a material that has been subjected to cold working, and wherein the cold working of the latch of the at least one appliance of the second set is carried out for a higher percentage of cold working than the percentage of the cold working of the latch of the at least one appliance of the first set.

16. An orthodontic brace according to claim 9 wherein the brace includes an orthodontic archwire connected to at least some of the appliances of the first set and the second set, wherein the archwire has a labial side with a concave portion when received in the archwire slots of the appliances, and wherein the certain value is greater for at least one appliance adjacent the concave portion of the archwire than the certain value of at least one remaining appliance of the brace.

17. An orthodontic brace comprising a first set of orthodontic appliances, a second set of orthodontic appliances and an orthodontic archwire connected to the first and second sets of orthodontic appliances, wherein each appliance has a base, a body extending from the base, an archwire slot extending across the body in a generally mesial-distal direction, and a latch connected to the body for releasably retaining the archwire in the archwire slot, wherein the latch releases the archwire from the archwire slot whenever the archwire exerts a force on the latch that exceeds a certain value, wherein the archwire has a labial side with a concave portion when received in the archwire slots of the appliances, and wherein the second set of appliances includes at least one appliance that is adjacent the concave portion of the archwire, wherein the first set of appliances includes the remaining appliances of the base, and wherein the certain value is greater for at least one appliance of the second set than the certain value of at least one appliance of the first set.

18. An orthodontic brace according to claim 17 wherein the brace includes a force module, and wherein at least one appliance of the second set is located next to the force module.

19. An orthodontic brace according to claim 17 wherein each latch comprises a mesial clip and a distal clip, each clip having an overall, generally "C"-shaped configuration and comprising a first section, a second section opposed to the first section and a third section interconnecting the first section and the second section, each clip also having a first arm portion connected to the first section remote from the third section and a second arm portion connected to the second section remote from the third section, and wherein the first section and the second section of the mesial clip and the distal clip of the at least one appliance of the second set have a thickness that is greater than the thickness of the first section and the second section of the at least one appliance of the first set.

20. An orthodontic brace according to claim 17 wherein each latch comprises a mesial clip and a distal clip, each clip having an overall, generally "C"-shaped configuration and comprising a first section, a second section opposed to the first section and a third section interconnecting the first section and the second section, each clip also having a first arm portion connected to the first section remote from the third section and a second arm portion connected to the second section remote from the third section, and wherein the first section and the second section of the mesial clip and the distal clip of the at least one appliance of the second set have a width that is greater than the width of the first section and the second section of the at least one appliance of the first set.

21. An orthodontic brace according to claim 17 wherein each latch is made of a material having a certain composition, and wherein the composition of the latch of at least one appliance of the second set is different of the composition of the latch of the at least one appliance of the first set.

22. An orthodontic brace according to claim 17 wherein each latch is made of a material subjected to heat treatment, and wherein the heat treatment of the latch of the at least one appliance of the second set is carried out at a different time and/or temperature than the heat treatment of the latch of the at least one appliance of the first set.

23. An orthodontic brace according to claim 17 wherein each latch is made of a material that has been subjected to cold working, and wherein the cold working of the latch of the at least one appliance of the second set is carried out for a higher percentage of cold working than the percentage of the cold working of the latch of the at least one appliance of the first set.

24. An orthodontic brace according to claim 17 wherein the brace includes an orthodontic archwire connected to at least some of the appliances of the first set and the second set, wherein the archwire has a labial side with a concave portion when received in the archwire slots of the appliances, and wherein the certain value is greater for at least one appliance adjacent the concave portion of the archwire than the certain value of at least one remaining appliance of the brace.

* * * * *

UNITED STATES PATENT AND TRADEMARK OFFICE
CERTIFICATE OF CORRECTION

PATENT NO. : 6,984,127 B2
DATED : January 10, 2006
INVENTOR(S) : Lai, Ming-Lai It is certified that error appears in the above-identified patent and that said Letters Patent is hereby corrected as shown below:

Column 11,
Line 6, delete "T1121" and insert -- TI121 --.

Signed and Sealed this

Twenty-first Day of March, 2006

JON W. DUDAS
*Director of the United States Patent and Trademark Office*